United States Patent [19]
Audett et al.

[11] Patent Number: 5,879,701
[45] Date of Patent: *Mar. 9, 1999

[54] TRANSDERMAL DELIVERY OF BASIC DRUGS USING NONPOLAR ADHESIVE SYSTEMS AND ACIDIC SOLUBILIZING AGENTS

[75] Inventors: Jay Audett, Mountain View; Susan E. Bailey, San Leandro, both of Calif.

[73] Assignee: Cygnus, Inc., Redwood, Calif.

[ * ] Notice: The term of this patent shall not extend beyond the expiration date of Pat. No. 5,843,472.

[21] Appl. No.: 808,211

[22] Filed: Feb. 28, 1997

[51] Int. Cl.$^6$ ...................................................... A61F 13/02
[52] U.S. Cl. .......................................... 424/448; 424/449
[58] Field of Search ..................................... 424/448, 449

[56] References Cited

U.S. PATENT DOCUMENTS

| | | | |
|---|---|---|---|
| 4,915,950 | 4/1990 | Miranda | 424/448 |
| 5,198,223 | 3/1993 | Gale | 424/449 |
| 5,232,702 | 8/1993 | Pfister | 424/448 |
| 5,262,165 | 11/1993 | Govil et al. | 424/448 |
| 5,503,843 | 4/1996 | Santus | 424/448 |
| 5,523,094 | 6/1996 | Andrieu et al. | |
| 5,612,056 | 3/1997 | Jenner et al. | 424/449 |
| 5,633,009 | 5/1997 | Kenealy | 424/448 |

FOREIGN PATENT DOCUMENTS

| | | |
|---|---|---|
| 0760238 A1 | 3/1997 | European Pat. Off. . |
| 0 582 502 A1 | 2/1994 | France . |
| 93/03697 | 3/1993 | WIPO . |
| 97/09985 | 3/1997 | WIPO . |

OTHER PUBLICATIONS

Aungst et al. (1990), "Contributions of Drug Solubilization, Partitioning, Barrier Disruption, and Solvent Permeation to the Enhancement of Skin Permeation of Various Compounds with Fatty Acids and Amines," *Pharmaceutical Research* 7(7):712–718.

Kim et al. (1996), "Transdermal Delivery of Dideoxynucleoside–Type Anti–HIV Drugs. 2. The Effect of Vehicle and Enhancer on Skin Permeation," *Journal of Pharmaceutical Science* 85(2):214–219.

Kim et al. (1995), "Transdermal Delivery of Zalcitable: In Vitro Skin Permeation Study," *AIDS* 9:1331–1336.

Jenner et al. (1995), "Transdermal Delivery of Physostigmine. A Pretreatment Against Organophosphate Poisoning," *J. Pharm. Pharmacol.* 47:206–212.

Lin et al. (1991), "The Effect of Plasticizers on Compatibility, Mechanical Properties, and Adhesion Strength of Drug–Free Eudragit E Films," *Pharmaceutical Research* 8(9):1137–1143.

Loftsson (1989), "Effect of Choline Esters and Oleic Acid on the Penetration of Acyclovir, Estradiol, Hydrocortisone, Nitroglycerin, Retinoic Acid and Trifluorothymidine Across Hairless Mouse Skin In Vitro,"0 *Acta Pharm. Nord.* 1(5):279–286.

Robinson et al. (1991), "Evaluation of the Primary Skin Irritation and Allergic Contact Sensitization Potential of Transdermal Tripolidine," *Fundamental and Applied Toxicology* 17:103–110.

Singh (1996), "Effect of Permeation Enhancers on the Release of Ketoprofen Through Transdermal Drug Delivery Systems," *Pharmazie* 51(10):741–744.

*Primary Examiner*—D. Gabrielle Brouillette
*Attorney, Agent, or Firm*—Angela P. Horne; Barbara G. McClung

[57] ABSTRACT

Solubilization enhancer compositions are provided which facilitate transdermal administration of basic drugs from transdermal systems composed of nonpolar adhesive materials. Preferred solubilization enhancer compositions are comprised of liquid, isomeric acid mixtures such as oleic acid dimer. The invention also relates to novel transdermal systems, drug reservoirs, formulations, and methods of drug administration, in which the disclosed solubilization enhancer compositions are used.

33 Claims, 3 Drawing Sheets

TRANSDERMAL DELIVERY OF BASIC DRUGS USING NONPOLAR ADHESIVE SYSTEMS AND ACIDIC SOLUBILIZING AGENTS

TECHNICAL FIELD

This invention relates generally to transdermal drug delivery, and more particularly relates to drug delivery systems for administering basic drugs transdermally, to drug reservoirs contained in such systems, to methods for administering basic drugs transdermally, and to pharmaceutical compositions formulated to administer basic drugs transdermally.

BACKGROUND

The delivery of drugs through the skin provides many advantages; primarily, such a means of delivery is a comfortable, convenient and noninvasive way of administering drugs. The variable rates of absorption and metabolism encountered in oral treatment are avoided, and other inherent inconveniences—e.g., gastrointestinal irritation and the like—are eliminated as well. Transdermal drug delivery also makes possible a high degree of control over blood concentrations of any particular drug.

Skin is a structurally complex, relatively thick membrane. Molecules moving from the environment into and through intact skin must first penetrate the stratum corneum and any material on its surface. They must then penetrate the viable epidermis, the papillary dermis, and the capillary walls into the blood stream or lymph channels. To be so absorbed, molecules must overcome a different resistance to penetration in each type of tissue. Transport across the skin membrane is thus a complex phenomenon. However, it is the cells of the stratum corneum which present the primary barrier to absorption of topical compositions or transdermally administered drugs. The stratum corneum is a thin layer of dense, highly keratinized cells approximately 10–15 microns thick over most of the body. It is believed to be the high degree of keratinization within these cells as well as their dense packing which creates in most cases a substantially impermeable barrier to drug penetration.

In order to increase skin permeability, and in particular to increase the permeability of the stratum corneum (i.e., so as to achieve enhanced penetration, through the skin, of the drug to be administered transdermally), the skin may be pretreated with a penetration enhancing agent (or "permeation enhancer", as sometimes referred to herein) prior to application of a drug; alternatively, a drug and a permeation enhancer are concurrently delivered.

The rate at which transdermal drug delivery occurs can be expressed as skin flux, i.e., as a quantity of drug which passes through a unit of skin surface area per unit time. Skin flux is affected by several factors, one of which is skin permeability.

Another factor which affects skin flux is the solubility of the drug in the reservoir in which it is contained. In certain kinds of transdermal systems, where the drug is only poorly soluble in the reservoir, skin flux varies over time; that is, while initially drug flux is well above the minimum value required to obtain pharmaceutically effective levels of the drug, flux subsequently declines to a point below the target value.

This effect is especially problematic in cases where steady state delivery of a drug over an extended time period is desired. A method for overcoming this problem, and obtaining a steady-state flux profile, is to solubilize a higher percentage of the drug in the reservoir. Doing so reduces the initial flux rate, and consequently increases the flux at later times, owing to the higher concentration of dissolved drug remaining in the reservoir; the net result is improved steady state delivery.

The present invention is directed to a novel method and composition for enhancing the solubilization of a drug in the drug reservoir in which it is contained. The invention is premised on the discovery that adding certain acidic agents to the drug reservoir enhances the solubility of the drug in the reservoir and thus improves steady state delivery of the drug.

DISCLOSURE OF THE INVENTION

Accordingly, it is an object of the present invention to provide a drug delivery system for the transdermal administration of a basic drug, comprising a laminated composite of a backing layer and at least one polymeric reservoir layer comprising the drug and a solubilization enhancing composition as will be described in detail herein.

It is another object of the invention to provide a drug reservoir for use in a transdermal system for delivering basic drugs.

It is still another object of the invention to provide a method for increasing the steady state flux of a basic drug through the skin which comprises transdermally administering the drug in combination with a solubilization enhancing amount of a solubilization enhancing composition as will be described in detail herein.

It is yet another object of the invention to provide a composition of matter for delivering a drug through the skin at a therapeutically effective flux over a predetermined time period comprising (a) a therapeutically effective amount of a basic drug; (b) a solubilization enhancing composition; and (c) a vehicle suited to transdermal drug administration.

Additional objects, advantages and novel features of the invention will be set forth in part in the description which follows, and in part will become apparent to those skilled in the art upon examination of the following, or may be learned by practice of the invention.

MODES FOR CARRYING OUT THE INVENTION

Figure 1:
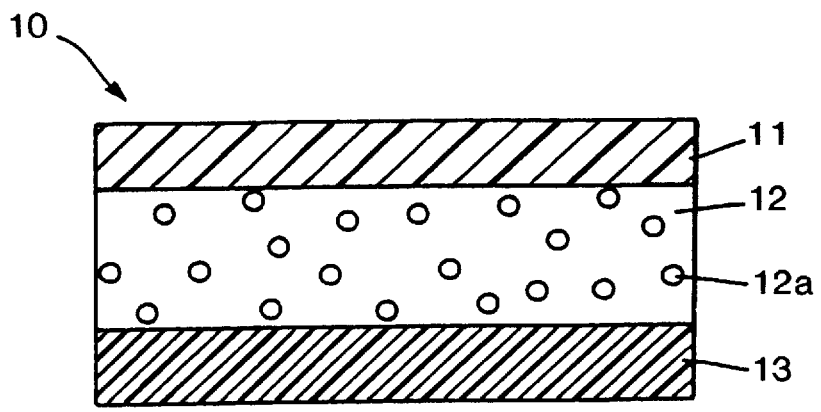
FIG. 1 illustrates in schematic form one embodiment of a transdermal delivery system which may be used in conjunction with the present invention.

Before describing the present invention in detail, it is to be understood that this invention is not limited to particular drugs, formulations or transdermal systems as such may, of course, vary. It is also to be understood that the terminology used herein is for the purpose of describing particular embodiments only, and is not intended to be limiting.

It must be noted that, as used in this specification and the appended claims, the singular forms "a", "an" and "the" include plural referents unless the content clearly dictates otherwise. Thus, for example, reference to "a permeation enhancer" includes a mixture of two or more permeation enhancers, reference to "a carrier" or "a vehicle" includes mixtures of carriers or vehicles, and the like.

Unless defined otherwise, all technical and scientific terms used herein have the same meaning as commonly understood by one of ordinary skill in the art to which the invention pertains. Although any methods and materials similar or equivalent to those described herein can be used in the practice of the present invention, the preferred materials and methods are described herein.

In describing and claiming the present invention, the following terminology will be used in accordance with the definitions set out below.

By "transdermal" delivery, applicants intend to include both transdermal (or "percutaneous") and transmucosal administration, i.e., delivery by passage of a drug through the skin or mucosal tissue and into the bloodstream.

"penetration enhancement" or "permeation enhancement" as used herein relates to an increase in the permeability of skin to a pharmacologically active agent, i.e., so as to increase the rate at which the drug permeates through the skin and enters the bloodstream. The enhanced permeation effected through the use of such enhancers can be observed by measuring the rate of diffusion of drug through animal or human skin using a diffusion cell apparatus as described in the Examples herein.

"Solubilization enhancement" as used herein relates to an increase in the solubility of drug formulation components in the drug reservoir, including but not limited to the drug itself, so as to obtain steady state drug delivery. The effect of enhanced solubilization on drug delivery can be observed by plotting the drug delivery profile obtained by measuring the rate of diffusion through animal or humans skin using a diffusion cell apparatus, as described in the Examples herein.

"Carriers" or "vehicles" as used herein refer to carrier materials suitable for transdermal drug administration, and include any such materials known in the art, e.g., any liquid, gel, solvent, liquid diluent, solubilizer, or the like, which is nontoxic and which does not interact with other components of the composition in a deleterious manner. The term "carrier" or "vehicle" as used herein may also refer to stabilizers, crystallization inhibitors, dispersing agents or other types of additives useful for facilitating transdermal drug delivery. It will be appreciated that compounds classified as "vehicles" or "carriers" may sometimes act as permeation enhancers, and vice versa, and, accordingly, these two classes of chemical compounds or compositions may sometimes overlap.

By "isomeric acid mixture" is meant a composition which includes two isomers of a single acid, i.e., two compounds which have identical chemical compositions but different geometric configurations.

By "pharmaceutically acceptable" is meant a material which is not biologically or otherwise undesirable, i.e., the material may be administered to an individual along with the desired drug formulation without causing any undesirable biological effects or interacting in a deleterious manner with any of the components of the drug reservoir in which it is contained.

By the term "pharmacologically active agent" or "drug" is meant chemical material or compound suitable for transdermal or transmucosal administration which induces a desired systemic effect. Such substances include the broad classes of compounds normally delivered through body surfaces and membranes, including skin. In general, this includes: anti-infectives such as antibiotics and antiviral agents; analgesics and analgesic combinations; anorexics; antihelminthics; antiarthritics; antiasthmatic agents; anticonvulsants; antidepressants; antidiabetic agents; antidiarrhoeals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmic; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers. The invention is, however, primarily directed to the transdermal administration of basic drugs, as the solubilizing compositions herein have been found to be particularly useful in facilitating delivery of basic drugs using transdermal systems composed of nonpolar materials. Examples of specific basic drugs include, but are not limited to, tamsulosin, olanzapine, prazosin, terazosin, phentolamine, phenoxybenzamine, alfuzosin and Rec 15/2739.

By "therapeutically effective" amount is meant a nontoxic but sufficient amount of a compound to provide the desired therapeutic effect, i.e., a dose of a drug which is effective in relieving symptoms of the condition or disease being treated.

An "effective" amount of a permeation enhancer composition as used herein means an amount that will provide the desired increase in skin permeability and, correspondingly, the desired depth of penetration, rate of administration, and amount of drug delivered.

An "effective" amount of a solubilization enhancer composition as used herein means an amount that will provide the desired increase in solubility of drug formulation components in the drug reservoir and, correspondingly, the desired rate of administration and amount of drug delivered.

By a "nonpolar" molecule or material is meant one which has no permanent electric dipole moment and therefore has no tendency to interact with polar molecules or materials.

By "predetermined area of skin" is intended a defined area of intact unbroken living skin or mucosal tissue. That area will usually be in the range of about 5 $cm^2$ to about 100 $cm^2$, more usually in the range of about 10 $cm^2$ to about 100 $cm^2$, still more usually in the range of about 20 $cm^2$ to about 60 $cm^2$. However, it will be appreciated by those skilled in the art of transdermal drug delivery that the area of skin or mucosal tissue through which drug is administered may vary significantly, depending on patch configuration, dose, and the like.

The focus of the invention is on transdermal administration of a basic drug with a solubilization enhancing composition. The present solubilization enhancing composition has been found to be particularly useful in facilitating the administration of basic drugs using transdermal systems containing drug reservoirs comprised of nonpolar materials such as polyisobutylene adhesives or the like. The systems with which the invention is useful are typically transdermal "patches" worn for at least four days; however, the invention is most useful in connection with transdermal systems designed to be worn for on the order of seven days.

The solubilizing enhancing composition itself is preferably a liquid which is an isomeric acid mixture. Examples of suitable solubilizers include, but are not limited to, oleic acid dimer and neodecanoic acid, with oleic acid dimer particularly preferred. The solubilizer constitutes at least about 0.10 wt.% of the reservoir, and preferably represents on the order of 0.25 wt.% to 1.0 wt.% of the reservoir.

The solubilizing enhancing composition is particularly advantageous when used in conjunction with skin permeation enhancer compositions. Suitable enhancers include, but are not limited to, dimethylsulfoxide (DMSO), N,N-dimethyl-acetamide (DMA), decylmethylsulfoxide ($C_{10}$MSO), polyethylene glycol monolaurate (PEGML), propylene glycol (PG), PGML, glycerol monolaurate (GML), lecithin, the 1-substituted azacycloheptan-2-ones, particularly 1-n-dodecylcyclazacycloheptan-2-one (available under the trademark Azone® from Whitby Research Incorporated, Richmond, Va.), alcohols, and the like. The permeation enhancer may also be a vegetable oil as described in commonly assigned U.S. Pat. No. 5,229,130 to Sharma. Such oils include, for example, safflower oil, cotton seed oil and corn oil.

Preferred enhancers for use in combination with the present solubilizing compositions are those described in U.S. patent application Ser. Nos. 08/807,447 and 08/807,448, filed on even date herewith and entitled "TRANSDERMAL DRUG DELIVERY SYSTEM FOR THE ADMINISTRATION OF TAMSULOSIN, AND RELATED COMPOSITIONS AND METHODS OF USE" and "BUTYROLACTONE-BASED SKIN PERMEATION ENHANCER COMPOSITIONS AND ASSOCIATED METHODS AND TRANSDERMAL SYSTEMS." In the latter application, enhancers are provided which comprise butyrolactone or butyrolactone substituted with one or two hydroxyl, lower alkyl, lower alkoxy, halogen and/or amino substituents. In the former application, lipophilic enhancers are provided having the formula $[RCOO]_nR'$, wherein n is 1 or 2, R is $C_1$–$C_{16}$ alkyl optionally substituted with 1 or 2 hydroxyl groups, and R' is hydrogen or $C_1$–$C_{16}$ alkyl optionally substituted with 1 or 2 hydroxyl groups.

Within the group of enhancers defined by $[RCOO]_nR'$, a first subset of compounds are represented by the formula $[CH_3(CH_2)_mCOO]_nR'$ in which m is an integer in the range of 8 to 16, n is 1 or 2, and R' is a lower alkyl ($C_1$–$C_3$) residue that is either unsubstituted or substituted with one or two hydroxyl groups. Preferred enhancers within this group include an ester which is a lower alkyl ($C_1$–$C_3$) laurate (i.e., m is 10 and n is 1) such as "PGML." It will be appreciated by those skilled in the art that the commercially available material sold as "PGML" is typically although not necessarily a mixture of propylene glycol monolaurate itself, propylene glycol dilaurate, and either propylene glycol, methyl laurate, or both. Thus, the terms "PGML" or "propylene glycol monolaurate" as used herein are intended to encompass both the pure compound as well as the mixture that is typically obtained commercially. Also within this group is a second subset of compounds, namely, esters of fatty alcohols represented by the formula $CH_3(CH_2)_m$—O—CO—$CHR^1R^2$, in which $R^1$ and $R^2$ are independently hydrogen, hydroxyl, or lower alkyl ($C_1$–$C_3$), and m is as above. Particularly preferred enhancers within this group are lauryl lactate and myristyl lactate. In addition, a third subset of compounds within this group are analogous fatty acids, i.e., acids having the structural formula $CH_3(CH_2)_mCOOH$ where m is as above. A particularly preferred acid is lauric acid.

Other enhancer compositions are wherein a lipophilic compound as just described, particularly PGML, is combined with a hydrophilic compound, such as a $C_2$–$C_6$ alkanediol. One preferred hydrophilic enhancer within this group is 1,3-butanediol. Such enhancer compositions are described in detail in PCT Publication No. WO 95/05137, published Feb. 23, 1995. Another hydrophilic enhancer that may be included in these compositions is an ether selected from the group consisting of diethylene glycol monoethyl ether (Transcutol®) and diethylene glycol monomethyl ether. Such enhancer compositions are described in detail in U.S. Pat. Nos. 5,053,227 and 5,059,426 to Chiang et al., both of common assignment herewith. Butyrolactone may also be incorporated into the enhancer composition.

A particularly preferred enhancer composition for use in conjunction with the present solubilizing compositions, as provided herein, is a three-component composition containing: a lipophilic compound having the formula $[RCOO]_nR'$, wherein n, R and R' are as above, preferably a lipophilic compound having the formula $[CH_3(CH_2)_mCOO]_nR'$ or $CH_3(CH_2)_m$—O—CO—$CHR^1R^2$ in which m, n, R, $R^1$, and $R^2$ are as defined above; a fatty acid $CH_3(CH_2)_mCOOH$ in which m is as defined for the ester; and a hydrophilic compound selected from the group consisting of diethylene glycol monoethyl ether, diethylene glycol monomethyl ether, PG, 1,3-butanediol, and butyrolactones as described above. The relative amounts of the three components in this enhancer composition are preferably, although not necessarily, as follows: (1) about 1 to 20 wt. %, preferably 1 wt. % to 10 wt. %, more preferably 5 wt. %, of the lipophilic component; (2) about 1 wt. % to 20 wt. %, preferably about 6 wt. % to 10 wt. %, more preferably 7 wt. % of the fatty acid component; and (3) about 60 wt. % to 95 wt. %, preferably 70 wt. % to 90 wt. %, more preferably 85 wt. % of the hydrophilic component.

The amount of enhancer composition present in the drug formulation will depend on a number of factors, e.g., the strength of the particular enhancer composition, the desired increase in skin permeability, and the amount of drug which is necessary to deliver.

Other components that may be included in the drug formulation include carriers, tackifiers, pigments, dyes, and other additives that do not adversely affect the mechanical or adhesive properties of the formulation.

The method of delivery of the present compositions may vary, but necessarily involves application of the selected composition to a defined surface of the skin or other tissue for a period of time sufficient to provide the desired blood level of drug for the desired period of time. The method may involve direct application of the composition as an ointment, gel, cream, or the like, or may involve use of a drug delivery device as taught, for example, in U.S. Pat. Nos. 3,742,951, 3,797,494 and 4,568,343. The method may also, if desired, involve pre-treatment of the skin with an enhancer to increase the permeability of the skin to the applied drug.

A transdermal delivery system can be constructed with the enhancer composition described hereinabove to deliver drugs for sustained drug delivery. The targeted skin flux for delivery of a particular drug can be achieved by adjusting vehicle composition and vehicle loading, as well as by adjusting the surface area through which the compositions are administered to skin.

Preferred transdermal drug delivery systems for use herein contain one or more drug/permeation enhancer reservoirs, a backing layer, and optionally one or more additional layers as those skilled in the art of transdermal drug delivery will readily appreciate.

One type of drug delivery system for transdermally administering tamsulosin is shown in FIG. 1. The system is in the form of a laminated composite, generally designated 10, comprising a backing layer 11, a reservoir layer 12 containing drug 12a either dispersed therein, or adsorbed or absorbed by a particulate hydrophilic material, and a release liner 13.

The backing layer 11 functions as the primary structural element of the device and provides the device with much of its flexibility, drape and, preferably, occlusivity. The material used for the backing layer should be inert and incapable of absorbing drug, enhancer or other components of the pharmaceutical composition contained within the device. The backing is preferably made of one or more sheets or films of a flexible elastomeric material that serves as a protective covering to prevent loss of drug and/or vehicle via transmission through the upper surface of the device, and will preferably impart a degree of occlusivity to the device, such that the area of the skin covered on application becomes hydrated. The material used for the backing layer should permit the device to follow the contours of the skin and be worn comfortably on areas of skin such as at joints or other points of flexure, that are normally subjected to mechanical strain with little or no likelihood of the device disengaging from the skin due to differences in the flexibility or resiliency of the skin and the device. Examples of materials useful for the backing layer are polyesters, polyethylene, polypropylene, polyurethanes and polyether amides. The layer is preferably in the range of about 15 microns to about 250 microns in thickness, and may, if desired, be pigmented, metallized, or provided with a matte finish suitable for writing.

The reservoir layer 12 in FIG. 1 doubles as the means for containing drug and as an adhesive for securing the device to the skin during use. That is, as release liner 13 is removed prior to application of the device to the skin, reservoir layer 12 serves as the basal surface of the device which adheres to the skin. Reservoir layer 12 is comprised of a pressure-sensitive adhesive suitable for long-term skin contact. It must also be physically and chemically compatible with tamsulosin and the carriers and vehicles employed. Suitable materials for this layer include, for example, polybutylenes, polyisobutylenes, polybutadiene, polyethylene, styrene-butadiene copolymers, polyisoprene, ethylene/acrylic copolymers, silicones and their copolymers, and butadiene/acrylonitrile copolymers, gelled or thickened mineral oil, petroleum jelly and various aqueous gels and hydrophilic polymers that may serve as thickening agents. Preferred materials are nonpolar adhesives, and a particularly preferred material is polyisobutylene.

Release liner 13 is a disposable element which serves only to protect the device prior to application. Typically, the release liner is formed from a material impermeable to the drug, vehicle and adhesive, and which is easily stripped from the contact adhesive. Release liners are typically treated with silicone or fluorocarbons. Silicone-coated polyester is presently preferred.

In a variation on this embodiment, reservoir layer 12 comprises a matrix of a continuous hydrophobic polymer phase, with a particulate phase of a hydrated inorganic silicate and drug adsorbed or absorbed thereby. Such a system is described, for example, in PCT Publication No. WO94/07468, entitled "Two-Phase Matrix for Sustained Release Drug Delivery Device." As explained in that application, polymers which may be used as the continuous hydrophobic phase are polysiloxanes, polyisobutylene, solvent-based hydrophobic polyacrylates, polyurethanes, plasticised ethylene-vinyl acetate copolymers, low molecular weight polyether block amide copolymers, styrene-butadiene polymers, and vinyl acetate-based adhesives, with the hydrophobic polymer normally constituting about 30 wt. % to 95 wt. %, more typically 40 wt. % to 60 wt. %, of the matrix. The dispersed inorganic silicate is in the form of particulates that are typically in the non-colloidal size range of 0.001 to 0.1 mm, more usually 0.01 to 0.05 mm.

In another variation on this embodiment, a polymer reservoir is provided containing sorbent particles as described in commonly assigned U.S. patent application Ser. No. 08/374,422, entitled "Polymer Adhesive Formulation Containing Sorbent Particles," published through the PCT as WO 96/22084. In this case, the polymer used is an adhesive that is substantially free of functional groups and by itself has acceptable cold flow properties (e.g., silicones, polyisobutylene, block co-polymers of polystyrene and polybutadiene/polyisoprene).

Excessive cold flow may develop in transdermal matrix systems with high vehicle loadings. In the absence of other additives, the adhesive polymers may become plasticised by the vehicle. For this reason, porous sorbent materials are included in the adhesive. Sorbents typically constitute between 5% and 15% by weight of the components of the drug formulation, and are capable of absorbing about 10% to 50% by weight of these components. Examples of sorbent materials used for this purpose include porous silica gel, porous diatomaceous earth and sorptive nonwoven polymers. The polymer adhesives selected for use in the transdermal matrix system lack functional groups and are incapable of forming bonds with the sorbent particles.

The cold flow properties of the polymer adhesives of the present invention are considered acceptable when adhesion of the transdermal patch to the skin of the user remains high throughout the drug delivery period and the adhesive does not extend beyond the boundary of the patch.

Figure 2:
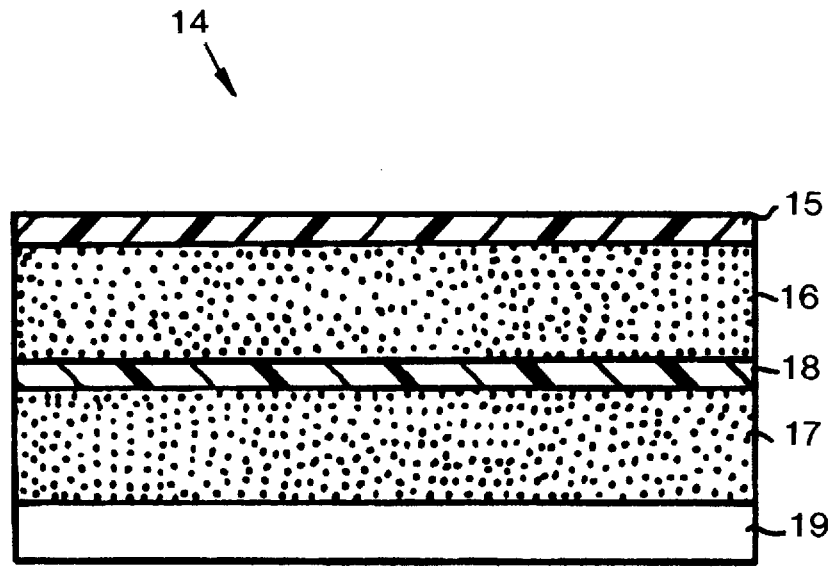
FIG. 2 illustrates in schematic form an alternative embodiment of a transdermal delivery system which may be used in conjunction with the present invention.

FIG. 2 illustrates a different type of laminated composite that may serve as the transdermal delivery system herein. That system is shown generally at 14, with backing layer 15, an upper, anchor adhesive layer 16, a lower contact adhesive 17, source layer 18 sandwiched between the two adhesive layers, and release liner 19. The backing layer and release liner are as described above with respect to the structure of FIG. 1. With regard to drug reservoir layers 16 and 17, suitable materials are as described above, e.g., polysiloxanes, polyisobutylenes, polyacrylates, polyurethanes, plasticised ethylene-vinyl acetate copolymers, low molecular weight polyether amide block polymers, tacky rubbers, and mixtures thereof.

The source layer 18 is a thin, flexible layer of an adsorbent material which provides the surface on which the drug formulation or components thereof are printed or otherwise deposited. The source layer allows a liquid formulation to be printed on its surface as a result of having surface properties not found in typical adhesive layers, and is positioned between the adhesive layers to eliminate adhesive cold flow. During fabrication, the drug and/or enhancer formulation is deposited in liquid form onto the source layer overlying the contact adhesive layer in a substantially uniform pattern. The source layer should be of a material capable of transiently adsorbing the formulation deposited thereon such that the formulation will not be displaced from the layer during the lamination process and its diffusibility into the adhesive layer in the assembled transdermal patch will not be impaired. For the foregoing reasons, a non-woven material such as polyethylene, polypropylene, polyamides, cotton, rayon or 100% non-woven polyester approximately 0.001" to 0.010" thick is preferred.

The adhesive reservoir layers in these systems will generally although not necessarily range in thickness from about 1 to about 25 mils, preferably in the range of approximately 1 to 15 mils. If two or more reservoir layers are used, the reservoir layers in combination should meet the aforementioned thickness criteria. However, the thickness of the reservoir will depend, however, on a variety of considerations, including the quantity of drug to be incorporated in the reservoir, desired patch size, and the like.

It will be appreciated by those skilled in the art that variations on the aforementioned systems can be provided wherein still additional drug reservoir layers are included, along with source layers, such as of nonwoven fabric, therebetween.

In any of these transdermal systems, it may be desirable to include a rate-controlling membrane in the device on the skin side of one or more of the drug reservoirs. The materials used to form such a membrane are selected to limit the flux of one or more components, i.e., enhancers, vehicles, and the like, contained in the drug formulation. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, and the like. A particularly preferred material useful to form the rate controlling membrane is ethylene-vinyl acetate copolymer.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

In the following experimental section, efforts have been made to ensure accuracy with respect to numbers used (e.g., amounts, temperature, etc.) but some experimental error and deviation should be accounted for. Unless indicated otherwise, temperature is in degrees C. and pressure is at or near atmospheric.

All patents, patent applications, and publications mentioned herein, both supra and infra, are hereby incorporated by reference.

Experimental

Materials

Tamsulosin free base was provided by Yamanouchi Pharmaceutical. The polyisobutylene (PIB) adhesive was formulated with GRAS components. All other chemicals were medical or reagent grade.

Preparation of Prototype Systems

The current system design is composed of two adhesive layers with one non-woven mat in the middle. Tamsulosin, fillers, additives, or solid enhancers were placed in a jar. Solvents were added to the dry components until the mixture was a thick slurry (approximately 3 times the weight of the filler used). The slurry was stirred using a high shear blade for 10–30 minutes to break up any large clumps. Pre-blended polyisobutylene solution was added to the drug-containing slurry which was then rotated for 12 hours to form a uniform adhesive mixture. The mixture was cast on a release liner with a Gardner knife. The cast films were dried at 80° C. for 1.5 hours to remove all the solvent. The non-woven mat was laminated onto one half of the adhesive films; a backing material was laminated onto the other half. Laminates were die cut to 30 $cm^2$ before spraying liquid vehicles. The vehicle combination solution was sprayed onto the non-woven side of the patch and then blotted with Kimwipes to remove excess vehicle. The backing/adhesive/non-woven was laminated to the release liner/adhesive coating after the non-woven was sprayed with the vehicle. The systems were stored in sealed pouchstock for at least three days prior to the skin flux studies to allow full equilibration.

Skin Permeation from Vehicles and Prototypes

Pre-treated human cadaver skin was mounted on the modified Franz diffusion cell for the permeation studies. The receiver chamber was filled with phosphate buffer, 7.5 mL, at pH 7.0. For permeation from enhancer vehicles. Tamsulosin-saturated vehicle combinations were placed in the donor chamber. For solid matrix systems, punched patches (⅜" diameter) were peeled off the release liner and the drug adhesive layer was placed onto the stratum corneum. Receiver solution samples (7.5 mL) were taken usually every 24 hours during the seven day flux experiment. Another 7.5 mL fresh buffer solution was added to refill the receiver. The concentration of Tamsulosin in the receiver solutions was quantified by HPLC analysis. Skin flux (mg/$cm^2$/hr) was calculated from the slope of the cumulative amount of drug penetrating through the skin versus time at the steady-state. For each formulation, three to six replicates were conducted.

HPLC Method

A reverse-phase HPLC (Shimadzu) with a 4.6×125 mm Nuclcosil 100 C18 column was used. The mobile phase was 27% acetonitrile and 73% 0.005N perchloric acid aqueous solution. The flow rate was at 0.9 mL/min with detection at 280 nm. The retention time of tamsulosin was approximately 5 minutes. The area under the peak was used to calculate the concentration and the range of the calibration curve was from 0.5 mg/mL to 20 mg/mL.

Results

Figure 3:
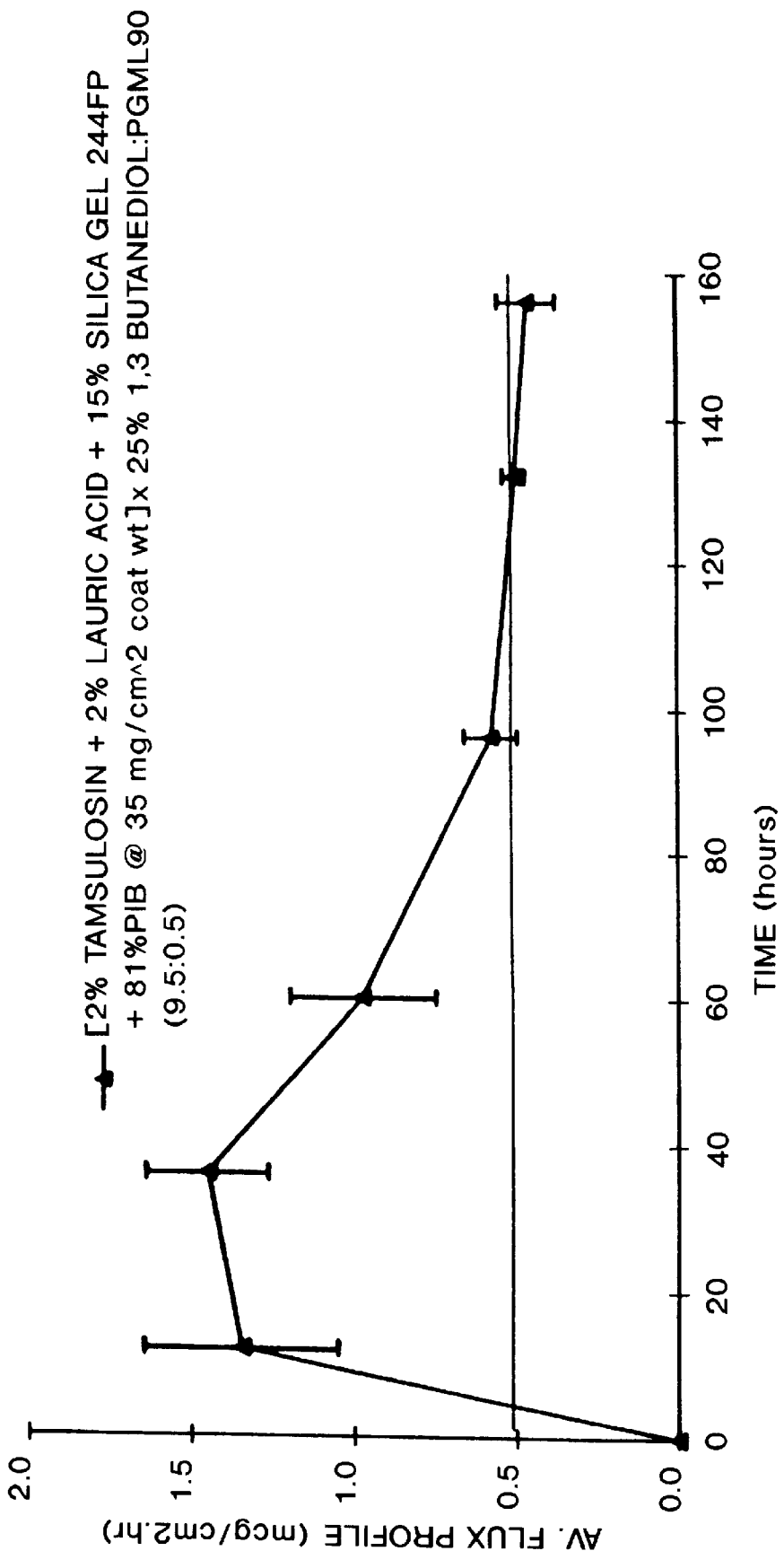
FIG. 3 is a skin flux profile obtained for tamsulosin in a formulation that does not include a solubilization enhancer composition.
Figure 4:
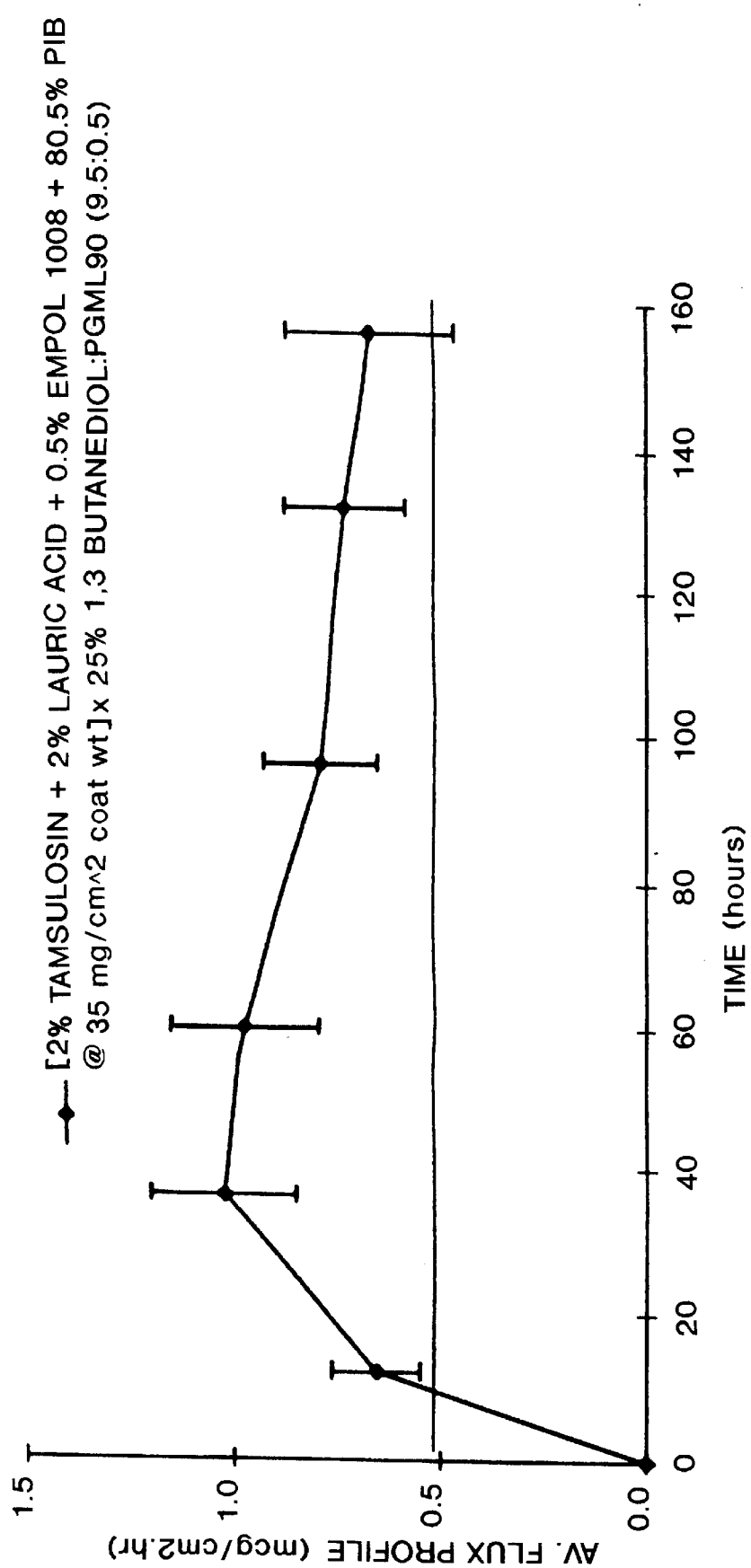
FIG. 4 is a skin flux profile obtained for a tamsulosin formulation that includes a solubilization enhancer composition.

FIGS. 3 and 4 illustrate the results of the above flux studies using different enhancer and solubilizer compositions.

FIG. 3 illustrates the flux profile obtained for a composition containing 2% tamsulosin, 2% lauric acid, 15% silica gel 244 FP, 81% polyisobutylene at a 35 mg/$cm^2$ coating weight, and 25% 1,3-butanediol:PGML90 (9.5:0.5). The line shown at 0.50 $\mu g/cm_2$ represents the minimum flux for a 30 $cm^2$ tamsulosin system. As may be seen, a higher skin flux was observed during the first two days of the study, followed by a gradual decline until the skin flux values fell below the minimum during the last day of the seven-day test.

FIG. 4 illustrates the results for a similar composition containing an oleic acid dimer ("EMPOL 1008" obtained from Henkel. The composition evaluated in this study was 2% tamsulosin, 2% lauric acid, 0.5% EMPOL 1008, 80.5% polyisobutylene at a 35 mg/$cm^2$ coating weight, and 25% 1,3-butanediol:PGML90 (9.5:0.5). Here, the initial skin flux was reduced because of the increased drug solubility in the adhesive matrix, while flux increased at later timepoints because of the higher concentration of dissolved drug. The net result here is improved steady state delivery with addition of only 0.5% oleic acid dimer as a solubilizing agent.

We claim:

1. A drug delivery system for the transdermal administration of a basic drug, comprising a laminated composite of:

a) a backing layer that is substantially impermeable to the drug; and b) at least one polymeric reservoir layer containing a formulation comprised of the drug and at least about 0.10 weight percent of a solubilization enhancing composition comprised of oleic acid dimer, neodecanoic acid, or a mixture thereof which is effective to facilitate solubilization of the drug in the polymeric reservoir layer, wherein the thickness of the system, the solubilization enhancer composition, and the amount of the solubilization enhancer composition are selected to provide for transdermal administration of the drug at a therapeutically effective flux over a predetermined time period.

2. The system of claim 1, wherein the solubilization enhancer composition is in the form of a liquid, isomeric acid mixture.

3. The system of claim 1, wherein the solubilization enhancer composition is comprised of oleic acid dimer.

4. The system of claim 1, wherein the solubilization enhancer composition is comprised of neodecanoic acid.

5. The system of claim 1, wherein the solubilization enhancer composition represents at least about 0.10 wt. % of the reservoir layer.

6. The system of claim 5, wherein the solubilization enhancer composition represents approximately 0.25 wt. % to 1.0 wt. % of the reservoir layer.

7. The system of claim 1, wherein the basic drug is selected from the group consisting of tamsulosin, olanzapine, prazosin, terazosin, phentolamine, phenoxybenzamine, alfuzosin, and Rec 15/2739.

8. The system of claim 7, wherein the basic drug is tamsulosin.

9. The system of claim 8, wherein the therapeutically effective flux is at least about 0.50 $\mu g/cm^2/hr$.

10. The system of claim 1, wherein the predetermined time period is at least about four days.

11. The system of claim 1, wherein the predetermined time period is approximately seven days.

12. The system of claim 1, wherein the reservoir layer is comprised of pharmaceutically acceptable, nonpolar adhesive material.

13. The system of claim 12, wherein the adhesive material is polyisobutylene.

14. The system of claim 1, wherein the reservoir layer further includes a skin permeation enhancer composition $[RCOO]_nR'$, wherein n is 1 or 2, R is $C_1$–$C_{16}$ alkyl optionally substituted with 1 or 2 hydroxyl groups, and R' is hydrogen or $C_1$–$C_{16}$ alkyl optionally substituted with 1 or 2 hydroxyl groups.

15. The system of claim 14, wherein the skin permeation enhancer composition comprises: an ester component having the formula $[CH_3(CH_2)_mCOO]_nR'$ in which m is an integer in the range of 8 to 16, n is 1 or 2, and R' is a lower alkyl ($C_1$–$C_3$) residue that is either unsubstituted or substituted with one or two hydroxyl groups; an acid component having the formula $CH_3(CH_2)_mCOOH$ where m is as defined previously; and an ether component selected from the group consisting of diethylene glycol monoethyl ether, diethylene glycol monomethylether, butyrolactone, and butyrolactone substituted with one or two substituents selected from the group consisting of lower alkyl, lower alkoxy, halogen and amino substituents.

16. A transdermal drug reservoir comprised of:
(a) a drug formulation containing a basic drug,
(b) at least about 0.10 weight percent of a solubilization enhancing composition comprised of oleic acid dimer, neodecanoic acid, or a mixture thereof which is effective to facilitate solubilization of the drug in the reservoir, in (c) a nonpolar polymeric adhesive material, wherein the solubilization enhancing composition and the amount of the solubilization enhancing composition are selected to provide for transdermal administration of the drug at a therapeutically effective flux over a predetermined time period.

17. The drug reservoir of claim 16, wherein the solubilization enhancer composition is in the form of a liquid, isomeric acid mixture.

18. The drug reservoir of claim 16, wherein the solubilization enhancer composition is comprised of oleic acid dimer.

19. The drug reservoir of claim 16, wherein the solubilization enhancing composition represents approximately 0.25% to 1.0% by weight of the reservoir layer.

20. The drug reservoir of claim 16, wherein the basic drug is selected from the group consisting of tamsulosin, olanzapine, prazosin, terazosin, phentolamine, phenoxybenzamine, alfuzosin, and Rec 15/2739.

21. The drug reservoir of claim 20, wherein the basic drug is tamsulosin.

22. The drug reservoir of claim 21, wherein the therapeutically effective flux is at least about 0.50 $\mu g/cm^2/hr$.

23. The drug reservoir of claim 16, wherein the predetermined time period is at least about four days.

24. The drug reservoir of claim 16, wherein the predetermined time period is approximately seven days.

25. The drug reservoir of claim 16, wherein the adhesive material layer is comprised of polyisobutylene.

26. The drug reservoir of claim 16, wherein the adhesive material further includes a skin permeation enhancer composition $[RCOO]_nR'$, wherein n is 1 or 2, R is $C_1$–$C_{16}$ alkyl optionally substituted with 1 or 2 hydroxyl groups, and R' is hydrogen or $C_1$–$C_{16}$ alkyl optionally substituted with 1 or 2 hydroxyl groups.

27. The drug reservoir of claim 26, wherein the skin permeation enhancer composition comprises: an ester component having the formula $[CH_3(CH_2(CH_2)_mCOO]_nR'$ in which m is an integer in the range of 8 to 16, n is 1 or 2, and R' is a lower alkyl ($C_1$–$C_3$) residue that is either unsubstituted or substituted with one or two hydroxyl groups; an acid component having the formula $CH_3(CH_2)_mCOOH$ where m is as defined previously; and an ether component selected from the group consisting of diethylene glycol monoethyl ether, diethylene glycol monomethylether, butyrolactone, and butyrolactone substituted with one or two substituents selected from the group consisting of lower alkyl, lower alkoxy, halogen and amino substituents.

28. A method for achieving steady state flux of a basic drug through the skin, comprising:
transdermally administering the drug from a drug reservoir comprising at least about 0.10 weight percent of a solubilization enhancing composition comprised of oleic acid dimer, neodecanoic acid, or a mixture thereof,
wherein the solubilization enhancing composition is selected to provide for transdermal administration of the drug at therapeutically effective flux over a predetermined time period.

29. The method of claim 28, wherein the solubilization enhancing composition comprises a liquid, isomeric acid mixture.

30. The method of claim 28, wherein the solubilization enhancer composition is comprised of oleic acid dimer.

31. A transdermal drug formulation comprising:
a) a therapeutically effective amount of a basic drug;
b) at least about 0.10 weight percent of a solubilization enhancer composition comprised of oleic acid dimer, neodecanoic acid, or a mixture thereof selected to provide for transdermal administration of the drug at a therapeutically effective flux over a predetermined time period; and c) a vehicle suited to transdermal drug administration.

32. The formulation of claim 31, wherein the solubilization enhancing composition comprises a liquid, isomeric acid mixture.

33. The formulation of claim 31, wherein the solubilization enhancer composition is comprised of oleic acid dimer.

* * * * *